(12) United States Patent
Rahi et al.

(10) Patent No.: US 8,709,072 B2
(45) Date of Patent: Apr. 29, 2014

(54) ENDOPROSTHESIS

(75) Inventors: Mourad Rahi, Maple Grove, MN (US); Liliana Atanasoska, Edina, MN (US); Rajesh Radhakrishnan, Maple Grove, MN (US); Robert W. Warner, Woodbury, MN (US); Barry Cool, White Bear Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 238 days.

(21) Appl. No.: 13/106,477

(22) Filed: May 12, 2011

(65) Prior Publication Data

US 2011/0282436 A1  Nov. 17, 2011

Related U.S. Application Data

(60) Provisional application No. 61/334,355, filed on May 13, 2010.

(51) Int. Cl.
*A61F 2/82* (2013.01)

(52) U.S. Cl.
USPC ........ 623/1.42; 623/1.46; 623/1.44; 623/1.38

(58) Field of Classification Search
USPC ............. 623/1.34, 1.38, 1.39, 1.4, 1.42, 1.43, 623/1.44, 1.45, 1.46, 1.49
See application file for complete search history.

(56) References Cited

U.S. PATENT DOCUMENTS

| | | | |
|---|---|---|---|
| 5,195,969 A | 3/1993 | Wang et al. | |
| 5,270,086 A | 12/1993 | Hamlin | |
| 5,366,504 A | 11/1994 | Andersen et al. | |
| 5,674,242 A | 10/1997 | Phan et al. | |
| 6,287,332 B1 | 9/2001 | Bolz et al. | |
| 6,726,712 B1 | 4/2004 | Raeder-Devens et al. | |
| 7,365,126 B2 | 4/2008 | Atanasoska et al. | |
| 2002/0004060 A1 | 1/2002 | Heublein et al. | |
| 2003/0003220 A1 | 1/2003 | Zhong et al. | |
| 2003/0185895 A1 | 10/2003 | Lanphere et al. | |
| 2004/0148002 A1* | 7/2004 | Cheng et al. | 623/1.11 |
| 2005/0251249 A1 | 11/2005 | Sahatjian et al. | |
| 2007/0196424 A1* | 8/2007 | Glauser et al. | 424/423 |
| 2010/0239512 A1* | 9/2010 | Morris et al. | 424/65 |

FOREIGN PATENT DOCUMENTS

WO  2008/020218  2/2008

OTHER PUBLICATIONS

Bureekaew et al., Sci Tech. Adv. Mater. 9 (2008), 014108.
Dinca and Long, Angew. Chem. Int. Ed. 47, 6766, (2008).
Dinca and Long, JACS, 127, 9376, (2005).
Eddaudi et al., Acc. Chem. Res. 2001, 34, 319.
Farha et al., J. Am. Chem. Soc. 2007, 129, 12680.
Ferrara, "Industrial Applications of Polyolefin-Based Nanocomposites," 1st National Conference of the Program for Nanotechnologies in the Chemical Industry, Milan, 64 pages, Oct. 2, 2007.
Fornes et al., "Modeling properties of nylon 6/clay nanocomposites using composite theories," Polymer, vol. 44, pp. 4993-5013, (2003).
Gleich et al., Nature 435, 1214-1217 (2005).

(Continued)

*Primary Examiner* — David Isabella
*Assistant Examiner* — Suba Ganesan
(74) *Attorney, Agent, or Firm* — Fish & Richardson P.C.

(57) ABSTRACT

A stent includes a MOF which adjusts pore size upon desorption or adsorption of organic molecules.

23 Claims, 4 Drawing Sheets

(56) References Cited

OTHER PUBLICATIONS

Han and Godard, J. Am. Chem. Soc. 2007, 129, 8422.

Horcajada et al, "Flexible Porous Metal-Organic Frameworks for a Controlled Drug Delivery," Journal of American Chemical Society, vol. 130, pp. 6780-6780, (2008).

Lee, Design of New Bio-Materials, Fluorous Peptides and Metal-Peptides Frameworks, Doctoral Dissertation (Chemistry), University of Michigan 2008.

Li and Yang, J. Am. Chem. Soc. 2006, 128, 8136.

Mantion et al., "Metal-Peptide Frameworks (MPFs): "Bioinspired" Metal Orgainic Frameworks," Journal of American Chemical Society, vol. 130, No. 8, pp. 2517-2526, (2008).

Nair et al., "Biodegradable polymers as biomaterials", Progress in Polymer Science, vol. 32, pp. 732-798, (2007).

Park et al., "Microstructural change and precipitation hardeningin melt-spun Mg—X—Ca alloys," Science and Technology of Advanced Materials, vol. 2, pp. 73-78, (2001).

Reiter et al., "Nanoscale Coordination Polymers for Platinum-Based Anticancer Drug Delivery," Journal of American Chemical Society, vol. 130, pp. 11584-11585, (2008).

Rieter et al., "Surface Modification and Functionalization of Nanoscale Metal-Organic Frameworks for Controlled Release and Luminescence Sensing," Journal of American Chemical Society, vol. 129, pp. 9853-9853, (2007).

Rowsell and Yaghi, J. Am. Chem. Soc. 2006, 128, 1304.

Shekhah, Langmuir 2007, 23, 7740.

Tanable et al., JACS 2008, 130, 8508-8517.

Taylor et al., JACS, 2008.

Wu et al., "A Homochiral Porous Metal—Organic Framework for Highly Enantioselective Heterogeneous Asymmetric Catalysis," Journal of American Chemical Society, vol. 127, pp. 8940-8941, (2005).

Yans et al., J. Ind. Eng. Chem., vol. 13, No. 4 (2007) 485-500.

Zhao et al., Energy Environ. Sci., 2008, 1, 222.

Zou et al., "Rational assembly of a 3D metal-organic framework for gas adsorption with predesigned cubic building blocks and 1D open channels," Chemical Communications, pp. 3526-3528, (2005).

* cited by examiner

○ Example of Drug molecule

⬠ Example of MOF

ENDOPROSTHESIS

CROSS-REFERENCE TO RELATED APPLICATION

This application claims priority under 35 USC §119(e) to U.S. Provisional Patent Application Ser. No. 61/334,355, filed on May 13, 2010, the entire contents of which are hereby incorporated by reference.

TECHNICAL FIELD

The present invention relates to endoprosthesis, and more particularly to stents.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprosthesis include stents, covered stents, and stent-grafts.

Endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism can include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

It is sometimes desirable for an implanted endoprosthesis to erode over time within the passageway. For example, a fully erodable endoprosthesis does not remain as a permanent object in the body, which may help the passageway recover to its natural condition. Erodible endoprosthesis can be formed from, e.g., polymeric material, such as polylactic acid, or from metallic material such as magnesium, iron or an alloy thereof.

SUMMARY

The present invention is directed to an endoprosthesis, such as, for example, a biodegradable stent.

In an aspect, the invention features a stent including a tubular body having a metal organic framework (MOF) which adjusts pore size upon desorption or adsorption of organic molecules.

Embodiments may also include one or more of the following. The MOF includes a therapeutic agent. The MOF has a loading weight ratio of about 1:1 or greater of therapeutic agent to MOF. The MOF is a coating on a stent substrate. The coating has a thickness of about 1 micron or less. The stent substrate is biostable. The stent substrate is bioerodible. The stent substrate is Fe or Mg. The coating is bioerodible. The coating has bioerodible ligands. The MOF ligands are lactate, glycolate, caprolactone or amino acid, terephthalate or alkoxides. The MOF is hydrophobic. The MOF includes a therapeutic agent effective to reduce thrombosis or restenosis. The MOF includes multiple different therapeutic agents. The agents are released from the MOF substantially in sequence. The therapeutic agent is a gas. The therapeutic agent is hydrogen, hydrogen sulfide, or Xe. The MOF includes Ti, Zr, Ta, Ru or Pt, Gd, Mn, Ba, Pt or Ir.

In another aspect, the invention features an implantable medical device. The medical device comprises an MOF including a therapeutic agent, a radiopaque element, magnetic particle imaging (MPI), and/or magnetic resonance imaging (MRI) visibility element.

The MOF is embedded in a matrix. The matrix defines the stent body. The MOF comprises two or more of a therapeutic agent, a radiopaque element, an MPI agent and an MRI visibility agent.

In another aspect the invention features a defibrillation lead comprising an MOF including a therapeutic agent.

In another aspect, the invention features a vascular closure device comprising a biodegradable anchor including an MOF.

In another aspect, the invention features a method comprising forming a tubular body including an MOF that provides high hydrogen bonding energy; and loading the MOF with a hydrogen antioxidant.

Embodiments may also include one or more of the following. The MOF is porous and the high hydrogen bonding energy is provided by reducing pore sizes. Reducing pore sizes comprises catenating two or more metal-organic frameworks. The high hydrogen bonding energy is provided by doping the MOF with cations or anions. The cations or anions comprise ammonium fluoride or lithium. The high hydrogen bonding energy is provided by doping the MOF with Pt or Pd.

Embodiments may include one or more of the following advantages. A stent is provided with advantageous drug delivery characteristics, mechanical properties, biodegradability, and/or MRI/fluoroscopic properties. The stent includes a MOF which is selected to deliver drug. The MOF can accommodate high drug loadings and selected drug release profiles. The MOF can be provided as a thin coating, which shows strong adherence to a stent body. The MOF can be biostable or bioerodible, which can be provided on a biostable or bioerodible stent body. A stent body can be formed of a MOF. The endoprosthesis may not need to be removed from a lumen after implantation. The endoprosthesis can have a low thrombogenecity and high initial strength. The endoprosthesis can exhibit reduced spring back (recoil) after expansion. Lumens implanted with the endoprosthesis can exhibit reduced restenosis. The endoprosthesis can be erodible.

The details of one or more embodiments are set forth in the accompanying drawings and the description below. Other features, objects, and advantages will be apparent from the description and drawings, and from the claims.

DESCRIPTION OF DRAWINGS

FIG. 2A is a perspective view of an embodiment of a stent, while

DETAILED DESCRIPTION

Figure 1A:
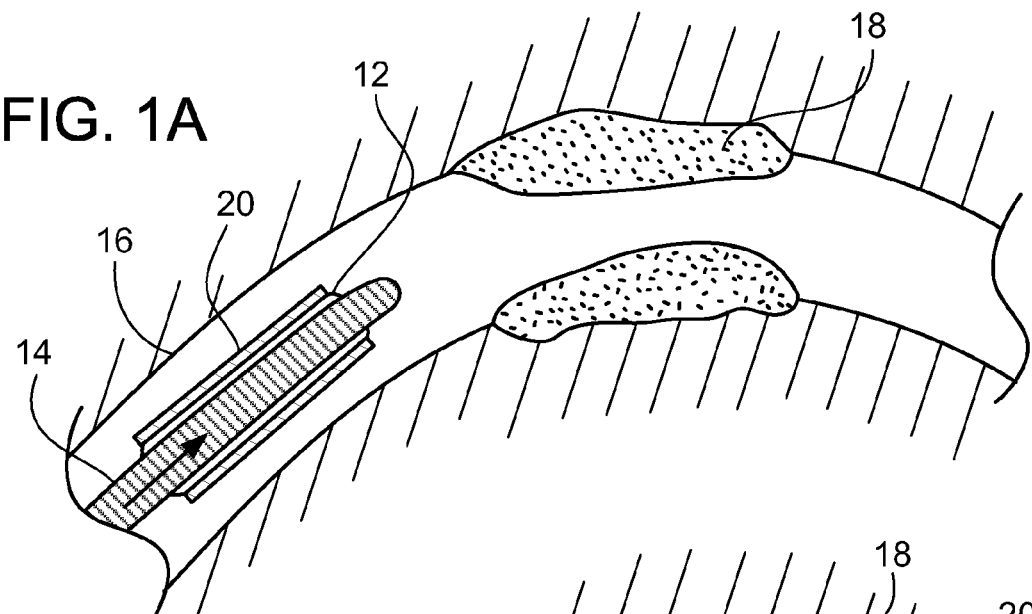
FIGS. 1A-1C are sequential, longitudinal cross-sectional views, illustrating delivery of an endoprosthesis in a collapsed state, expansion of the endoprosthesis, and the deployment of the endoprosthesis in a body lumen.
Figure 1B:
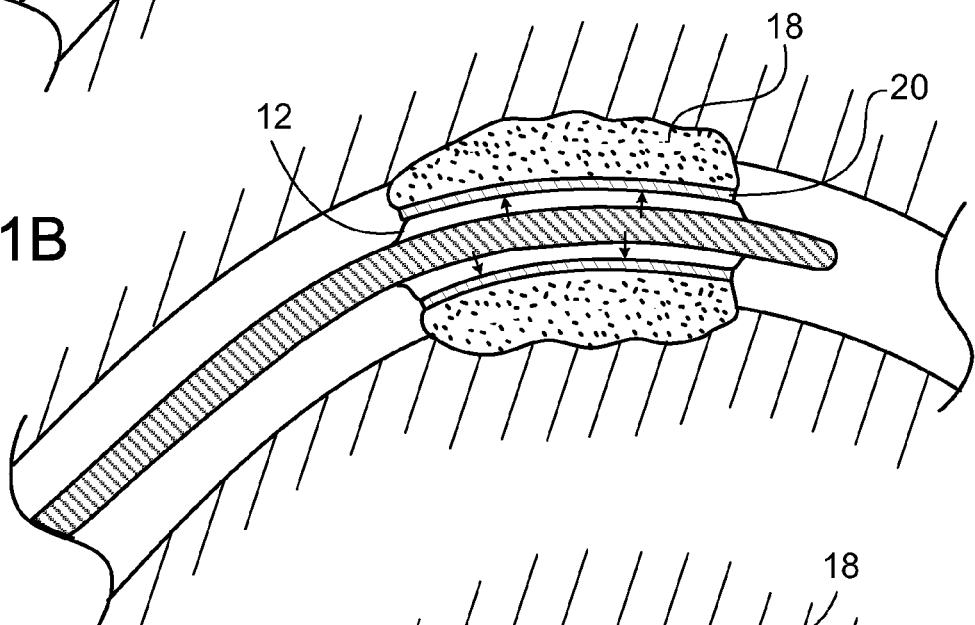
Figure 1C:
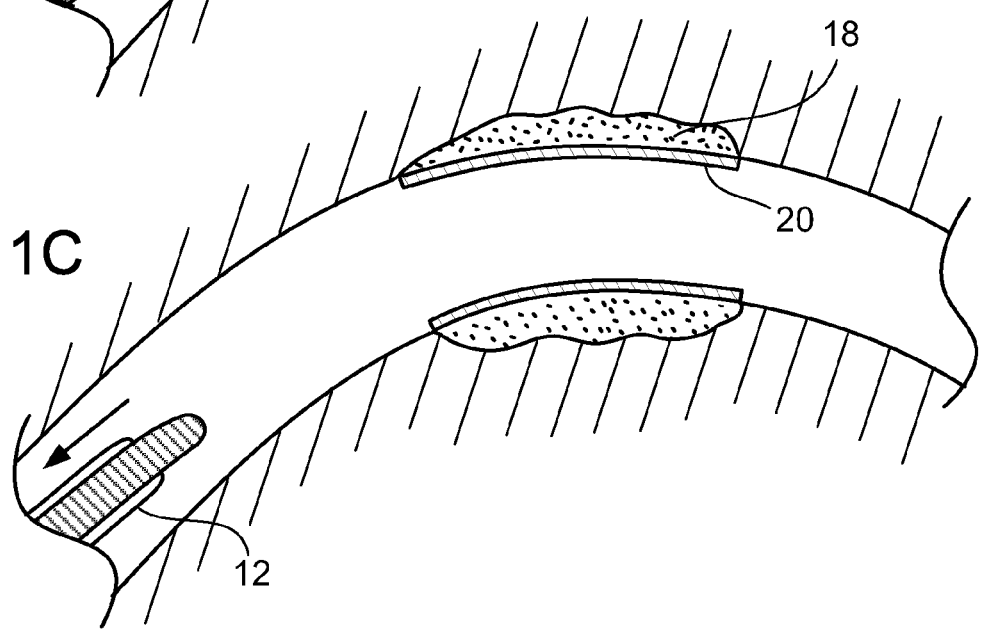

Referring to FIGS. 1A-1C, a stent 20 is placed over a balloon 12 carried near a distal end of a catheter 14, and is directed through the lumen 16 (FIG. 1A) until the portion carrying the balloon and stent reaches the region of an occlusion 18. The stent 20 is then radially expanded, e.g., by inflating the balloon 12, and compressed against the vessel wall with the result that occlusion 18 is compressed, and the vessel wall surrounding it undergoes a radial expansion (FIG. 1B). The pressure is then released from the balloon and the catheter is withdrawn from the vessel (FIG. 1C).

Figure 2A:
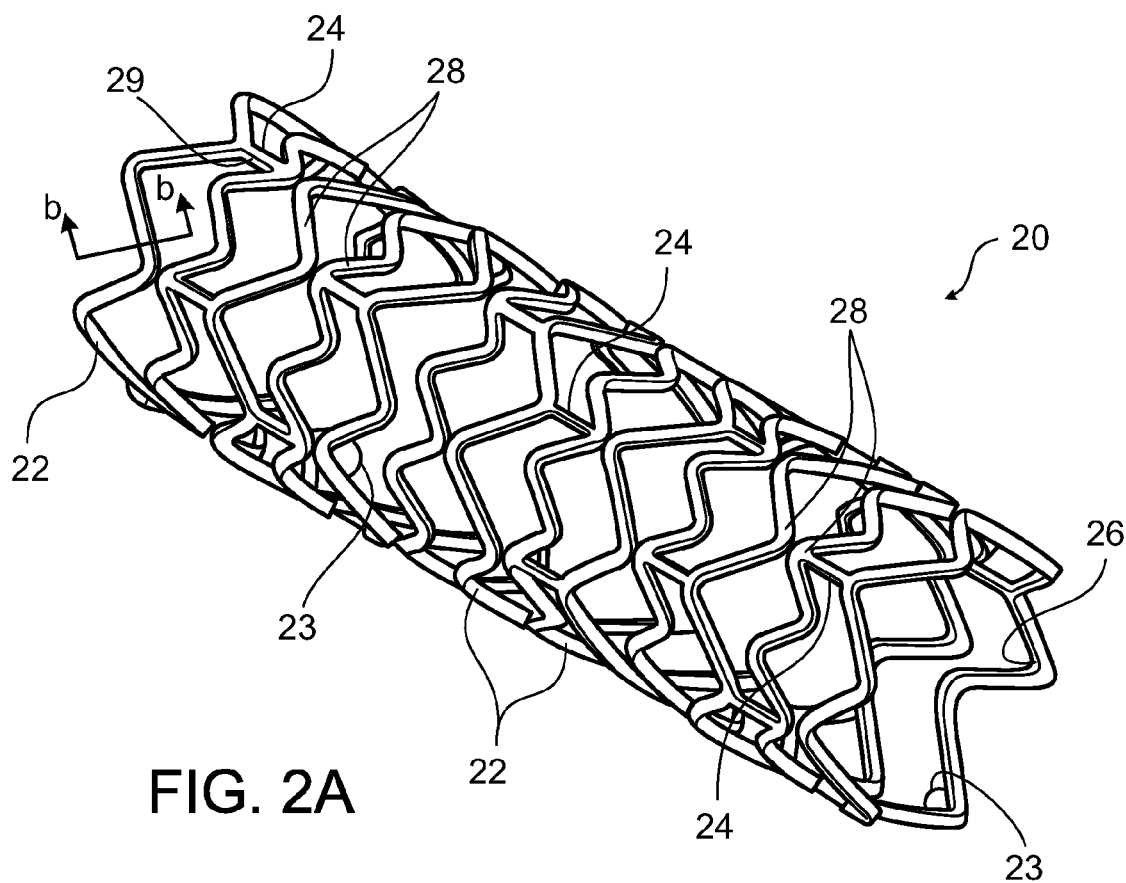

Referring to FIG. 2A, an expandable stent 20 can have a stent body having the form of a tubular member defined by a plurality of bands 22 and a plurality of connectors 24 that extend between and connect adjacent bands. During use, bands 22 can be expanded from an initial, smaller diameter to a larger diameter to contact stent 20 against a wall of a vessel, thereby maintaining the patency of the vessel. Connectors 24 can provide stent 20 with flexibility and conformability that allow the stent to adapt to the contours of the vessel. One or more bands 22 form acute angles 23. The angle 23 increases upon expansion of the stent. Stent body 20, bands 22 and connectors 24 can have a luminal surface 26, an abluminal surface 28, and a sidewall surface 29. In some embodiments, the bands and/or connectors, have a width, W, and a thickness, T, of about 50 to 150 microns. T and W can be selected based on known parameters suitable for stents.

Figure 2B:
FIG. 2B is a cross-section along line bb.

Referring to FIG. 2B, the stent body 30 carries a coating 32 including a therapeutic agent which is released to, for example, inhibit restenosis. The coating can have a thickness, Tc. In embodiments, the coating can carry a substantial load of drug and exhibit desirable agent release profiles, such as zero order release. As a result, the thickness Tc can be quite thin, which provides for an overall low drug release profile, and a good adhesion to the stent body surface with little foreign material introduced in the body. In embodiments, the thickness Tc of the coating is about 10 µm or less, e.g., 5 µm or 1 µm or less. In particular embodiments, the coating can be biodegradable. In FIG. 2B, the coating is illustrated on the abluminal surface. In embodiments, the coating may instead or in addition be on the luminal and/or side wall surfaces.

Figure 3A:
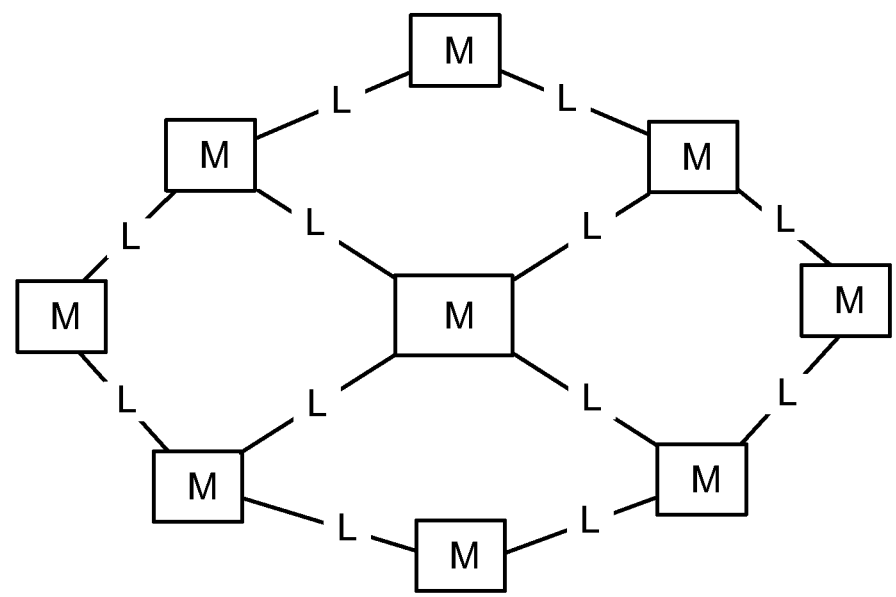
FIGS. 3A-3B are schematic drawings illustrating swelling of a metal organic framework.
Figure 3B:
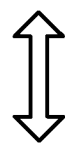
Figure 3B:
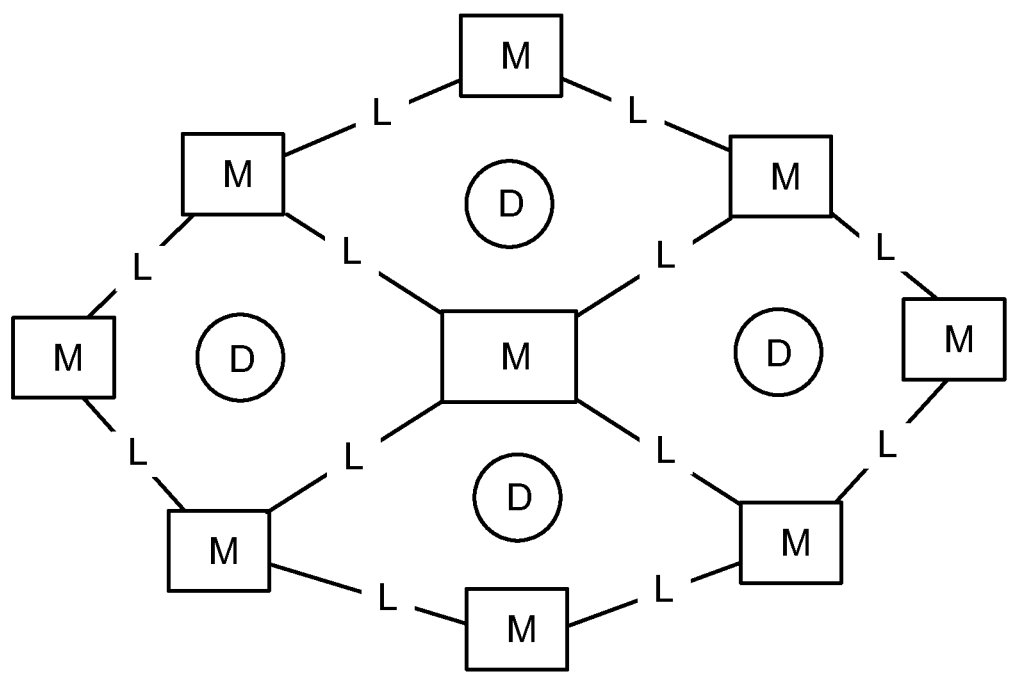

Referring to FIGS. 3A and 3B, the coating 32 and/or the stent body 30 is formed of a dynamic hybrid solid, such as a guest-shape responsive bioerodible metal-organic framework (MOF), which modulates or adjusts pore size in the framework upon adsorption and desorption of organic molecules in the pores of the framework. A MOF is a metal coordination compound where a polymer ligand, L, bridges between metal centers, M, and where each metal center binds to more than one ligand to create an array of metal centers. The MOF can swell on exposure to solvent and a therapeutic agent, D, such that the agent can be contained within the porous interstices of the MOF matrix. Mechanisms for pore size adjustment are described, for example, in Bureekaew et al., Sci Tech. Adv. Mater. 9 (2008), 014108.

For use in a stent, the MOF is selected to accommodate a drug, provide a desired release profile and drug loading, and have selected mechanical properties and bioerodibility or biostability. In embodiments, the MOF matrices are made of metals, such as Ti, Zr, Ta, W, Ir, Ru, Pt, and organic bridging ligands, such as terephtalates, alkoxides, amino acids and peptides, or others that enable their tunable flexible porosity by reversible swelling or breathing phenomenon. MOF and its breathing phenomenon are described in J. Am. Chem. Soc. 130 (8), 2517-2526 (2008).

The MOF is designed for stent use in coordination with the desired drug or delivery profile. For example, the size and swelling characteristics of the pores are selected in coordination with the size of the drug molecule. In addition, the hydrophobicity/hydrophilicy of the MOF is selected in coordination with the characteristics of the drug molecule. For example, for a hydrophobic drug molecule, such as paclitaxel or Everolimus, used for the treatment of restenosis, the MOF is made more hydrophobic to accommodate higher drug loadings. For a more hydrophilic drug species, such as Plavix, useful for treatment of thrombosis, a more hydrophilic MOF is used. The pore size and hydrophobicity/hydrophilicity of the MOF can be controlled by selection of suitable ligands. In particular embodiments, ligands including amino acids and peptides over a range of lengths and hydrophobicity characteristics can be utilized. Suitable techniques are described in Tanable et al., JACS 2008, 130, 8508-8517; Lee, Design of New Bio-Materials, Fluorous Peptides and Metal-Peptides Frameworks, Doctoral Dissertation (Chemistry), University of Michigan 2008. Suitable ligands are also described below.

The coating can include multiple sequential layers, one on top of another, of different MOFs and/or drug combinations. For example, an outer layer can be provided for initial release of an anti-thrombosis drug. An inner layer can be provided for subsequent, longer term release of an anti-restenosis drug. In addition, multiple different MOF-drug combinations can be provided at different locations along the stent, on luminal and abluminal surfaces, for example.

The MOF based drug eluting stent coatings can have high drug loading weight ratio on a drug to MOF basis. For example, the drug loading may be 0.5 µg drug/µg MOF, or more, such as 1.0 or 1.5 µg drug/µg MOF. Thin stent coatings can also be employed because of the MOF's high surface area (up to 3000 m$^2$/g) and high porosity. For active agents such as Everolimus, the high loading capacity of the polymer is highly beneficial. The thinner the polymer, the less risk of cohesive failure of the coating. In embodiments, the coating thickness is about 5 micron (µ) or less, e.g. about 1µ or 0.5µ or less or 0.01µ or more. Drug molecules of different sizes can be simultaneously loaded and released as a cocktail using the flexible porosity MOF matrix. Drug molecules can also be sequentially loaded and released from a layered MOF matrix. A time dependent release can be enhanced using a thin unloaded MOF layer separating drug loading compartments. Due to the breathing phenomenon, once the drug molecules in the topmost layer are released, the pores will shrink thus allowing for burst and slow release. Open internal pores allow complete elution of the active agents as opposed to polymers.

An MOF can be used to elute a gas, e.g., hydrogen antioxidant, hydrogen sulfide, Xe, for a vulnerable plaque treatment or reperfusion injury, e.g., myocardial (AMI), and cerebral (stroke). The MOF-based coating is designed to increase gas, e.g., hydrogen, binding energy at room temperature and optimize $H_2$ uptake by adsorption and release by desorption. The following approaches for hydrogen room temperature loading in the coating can be used:

i. Reduce MOF pore size and adjust geometry by ligand structure and functionalization; introduction of bulky groups in the organic ligands such as aromatics, carborane or trifluoro-methyl ii. Reduce MOF pore size by catenation in which two or more identical frameworks interpenetrate with each other iii. Form MOF matrices with coordinatively unsaturated metal sites based on Zn, Mn, Mg or other exposed metal ions iv. Dope MOF chemically with cations or anions such as ammonium fluoride or lithium v. Induce hydrogen "dissociation/spillover" by doping MOF with Pt, Pd or others.

Further discussion of hydrogen storage and therapeutic effects of hydrogen is in Zhao et al., *Energy Environ. Sci.*, 2008, 1, 222; Farha et al., *J. Am. Chem. Soc.* 2007, 129, 12680; Han and Godard, *J. Am. Chem. Soc.* 2007, 129, 8422; Li and Yang, *J. Am. Chem. Soc.* 2006, 128, 8136; Eddaudi et al., *Acc. Chem. Res.* 2001, 34, 319; and Rowsell and Yaghi, *J. Am. Chem. Soc.* 2006, 128, 1304.

To tune biodegradation, the matrices can include biodegradable metals such as Mg, Fe, Ca, Zn, Mn and alloys, and biodegradable organic linkers/bridging ligands such as, for example, lactate, glycolate, caprolactone, and amino acid. For example, to make a biodegradable MOF, poly-lactic acid (PLA)/metal-organic frameworks (MOF) composites can be used and loaded with drugs such as PTx, Everolimus and/or other therapeutic agents. Mechanical properties of biodegradable polymer stent can be controlled via metal polymer cross-linking and selection of suitable flexible organic ligands.

enhance cathodic sites which accelerates oxygen reduction. The MOF coating can be provided without a drug to control erosion or otherwise control the exposure of the stent body to body fluid.

Magnetic resonance imaging (MRI) visibility of the stent can be enhanced by using gadolinium (Gd) or manganese (Mn) to form the metal-organic frameworks. Radiopacity can be enhanced by using Ba, Pt, Ir metallo-organic species as a part of metal-organic frameworks; radiopacity can also be achieved with iodine functionality within the organic part of the framework. Magnetic particle imaging can be enhanced using magnetic particles such as superparamagnetic iron oxide (SPIO) particles, iron particles, ultra small particles, and ultra small superparamagnetic iron oxides (USPIO), e.g., 100 nm or less, such as 25 nm or less. Magnetic particle imaging is discussed further at http://bisl.berkeley.edu/index.php?n=mainmagneticparticleimaging; Goodwill et al., Society for Molecular Imaging, 2008, Nice, France; Gleich et al., Nature 435, 1214-1217 (2005).

The Metal-Organic Frameworks (MOFs) can be crystalline compounds with metal ions or clusters coordinated to organic molecules to form one-, two-, or three-dimensional structures. Suitable ligands for MOFs are further provided in the Table.

TABLE

| Common name | IUPAC name | Chemical formula |
|---|---|---|
| Bidentate Carboxylics | | |
| Oxalic acid | ethanedioic acid | HOOC—COOH |
| Malonic acid | propanedioic acid | HOOC—(CH$_2$)—COOH |
| Succinic acid | butanedioic acid | HOOC—(CH$_2$)$_2$—COOH |
| Glutaric acid | pentanedioic acid | HOOC—(CH$_2$)$_3$—COOH |
| Phthalic acid | benzene-1,2-dicarboxylic acid o-phthalic acid | C$_5$H$_4$(COOH)$_2$ |
| Isophthalic acid | benzene-1,3-dicarboxylic acid m-phthalic acid | C$_6$H$_4$(COOH)$_2$ |
| Terephthalic acid | benzene-1,4-dicarboxylic acid p-phthalic acid | C$_6$H$_4$(COOH)$_2$ |
| Tridentate Carboxylates | | |
| Citric acid | 2-Hydroxy-1,2,3-propanetricarboxylic acid | (HOOC)CH$_2$C(OH)(COOH)CH$_2$(COOH) |
| Trimesic acid | benzene-1,3,5-tricarboxylic acid | C$_9$H$_6$O$_6$ |
| Imidizoles | | |
| 1,2,3-Triazole | 1H-1,2,3-triazole | C$_2$H$_3$N$_3$ |
| pyrrodiazole | 1H-1,2,4-triazole | C$_2$H$_3$N$_3$ |
| Squaric acid | 3,4-Dihydroxy-3-cyclobutene-1,2-dione | C$_4$H$_2$O$_4$ |

The coating can be provided on a biostable stent formed, e.g., of stainless steel, or formed of a bioerodible stent formed, e.g., of Mg, Fe or polymers. Due to the breathing phenomenon, once the loaded drug molecules are released, the pores will shrink; the coating will become denser and will provide more corrosion protection for the stent body, e.g., Mg, if needed. The highly porous/high surface area MOF layer with rigid/inflexible organic linkers can be placed next to an iron stent surface to accelerate corrosion rate of Fe stent. The high surface area of the MOF can provide more sites for anodic or cathodic reaction. For example, the MOF can Frameworks can be prepared under reflux, precipitation, and re-crystallization, the vast majority of compounds have been discovered using hydrothermal synthesis techniques.

Carboxylates

Examples of such materials include metal salts of benzene-1,3,5-tricarboxylic acid (trimesic acid, BTC). A series of solid polymers can be made via the reaction of this tri-acid with salts of cobalt, manganese, zinc, cadmium, copper, lead, uranium and other metals. Other di- and tricarboxylic acids can be used. Pair of acids include 4,6-dinitro-5-hydroxyisophthalic acid and 2,4-dinitro-3-hydroxybenzoic acid which are formed by the reaction of a mixture of lead(II) nitrate, nickel nitrate, pyridine and 5-hydroxyisophthalic acid inside an autoclave. The resulting acids then form mixed lead/nickel polymers.

By using a non-bridging ligand such as 2,2'-bipyridine on a first row transition metal (such as zinc, manganese or cobalt) a less cross linked polymer can be obtained than that which is formed by the reaction of BTC and the simple metal salt in the absence of the non-bridging ligand. A solid formed using BTC is a layered solid where the benzene rings are coplanar with the planes. This is a layered solid which is similar to graphite in the fact that it is covalently bonded layers which are arranged on top of each other.

Polypyridines

Another synthetic method is to react a polypyridine whose geometry renders it unable to chelate metal atoms with all its nitrogen atoms. For instance 4,4'-bipyridine can be used to form polymers with many metals, e.g. cadmium. It is the case that cadmium nitrate reacts with a wide array of polypyridines to form different solids. Polypyridines can be used where the pyridine rings are separated by covalent spacers such as prop-1,3-diyl groups.

Another method of forming coordination polymers is to use a donor atom which bears more than one lone pair. For instance, this type of bridging has been seen in uranium fluorides and the lead carboxylates. MOF techniques are discussed further in Morris and Wheatley, WO2008/020218; Horcajada et al, *JACS* 2008, 130, 6780; Rieter et al., *JACS* 2007, 129, 9853; Rieter et al., *JACS* 2008, 103, 11584; and Wu et al., *JACS* 2005, 127, 8940, Bureekeaw et al. *Sci. Techn. Adv. Mater.* 9 (2008) 014108; Zou et al., *The Royal Society of Chem; Chem. Commun.* 2005, 3526-28. Biological linkers such as peptides, are discussed in Mantion, JACS 2008, 130(8), 2517-2526.

Other Embodiments

Figure 4:
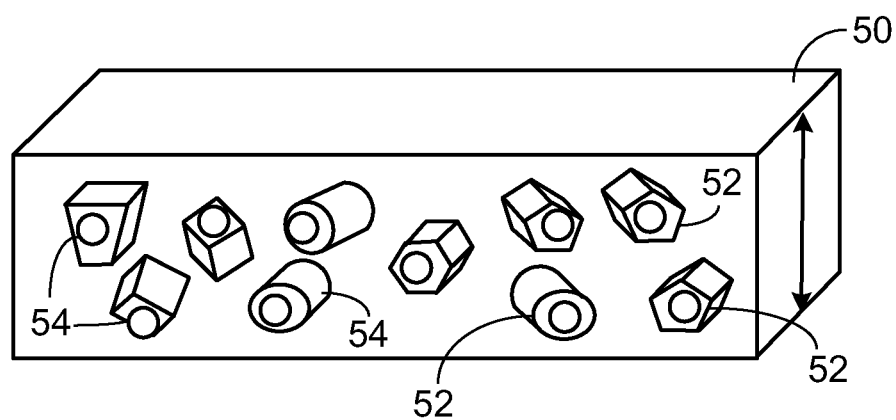
FIG. 4 is a schematic of a portion of a stent body.

Referring to FIG. 4, in embodiments, a suitable MOF can be embedded in a matrix of another material such as bioerodible material, e.g., a polymer, that is used as a stent body or a coating on a stent body. For example, a stent body 50 is formed of a biodegradable polymer such as PLA or PCL. Embedded within the body 50 are drug release domains 52, radiopaque doping 54, and MRI visibility domains. The domains are composed of MOFs. The radiopaque doping 54 can include radiopaque elements such as Ba, Pt, Ir or I. The MRI visibility domains can include MRI visible elements such as Gd or Mn. The matrix can provide a continuous, controlled drug delivery during the entire degradation of the stent body 50. The drugs loaded in the matrix can be highly three-dimensionally tunable, e.g., by controlling the ratio of the MOF amount to the amount of the biodegradable material in the stent body 50, and/or by controlling the ratio of the drug amount and the MOF amount. In some embodiments, mixtures of drugs can be loaded in the matrix to provide a drug cocktail delivery (e.g., delivering a mixture of drugs). Different drugs can be loaded into one or more selected MOFs.

The mechanical properties of the matrix can be adjusted by the use of nanocomposite fillers such as nanotubes, nanoclay or milled glass or talc. Suitable techniques are described in Fornes et al., *Polymer* 44 (2007) 4993-5013 and Ferrara Le Applicaionic Industrali di Nanocompositi a base di Paholefyne, Conferensa Nationale del Programma Nanotechalogic Industria Chimica, Milano, Oct. 2, 2007. Suitable bioerodible nanocompositions are described in Yans et al., *J. Ind. Eng. Chem.*, Vol. 13, No. 4 (2007) 485-500; Nair et al., *Prog. Polymer Sci.* 32, 762-798 (2007). Processing can be carried out by extrusion and laser cutting, and the drug can be pre- or post-loaded into the MOF.

In embodiments, multi-layer coatings or MOF nanoparticle cores stabilized with shells of amorphous silica or titania, which are capable of the time dependent release of drug molecules can be made by using processes such as Layer-by-Layer deposition or wet chemistry. Suitable techniques are described in Shekhah, *Langmuir* 2007, 23, 7740 and Reiter et al., *JACS* 2008, 130, 11584.

In some embodiments, biological molecules, such as peptides and others, can be used as a linker in the MOF. Description of using peptides as linkers in an MOF can be found in Mantion et al., J. Am. Chem. Soc. 130, 2517-2526 (2008). In some embodiments, the MOF can also be used for delivery of therapeutic agents from pacing and defibrillation leads. The MOF can also be used in vascular closure device, e.g., as a biodegradable anchor, or in a balloon.

According to this disclosure, a stent is bioerodible if the stent or a portion thereof exhibits substantial mass or density reduction or chemical transformation, after it is introduced into a patient, e.g., a human patient. Mass reduction can occur by, e.g., dissolution of the material that forms the stent and/or fragmenting of the stent. Chemical transformation can include oxidation/reduction, hydrolysis, substitution, and/or addition reactions, or other chemical reactions of the material from which the stent or a portion thereof is made. The erosion can be the result of a chemical and/or biological interaction of the stent with the body environment, e.g., the body itself or body fluids, into which it is implanted. The erosion can also be triggered by applying a triggering influence, such as a chemical reactant or energy to the stent, e.g., to increase a reaction rate. For example, a stent or a portion thereof can be formed from an active metal, e.g., Mg or Fe or an alloy thereof, and which can erode by reaction with water, producing the corresponding metal oxide and hydrogen gas; a stent or a portion thereof can also be formed from a bioerodible polymer, or a blend of bioerodible polymers which can erode by hydrolysis with water. Fragmentation of a stent occurs as, e.g., some regions of the stent erode more rapidly than other regions. The faster eroding regions become weakened by more quickly eroding through the body of the endoprosthesis and fragment from the slower eroding regions.

Preferably, the erosion occurs to a desirable extent in a time frame that can provide a therapeutic benefit. For example, the stent may exhibit substantial mass reduction after a period of time when a function of the stent, such as support of the lumen wall or drug delivery, is no longer needed or desirable. In certain applications, stents exhibit a mass reduction of about 10 percent or more, e.g., about 50 percent or more, after a period of implantation of about one day or more, about 60 days or more, about 180 days or more, about 600 days or more, or about 1000 days or less. Erosion rates can be adjusted to allow a stent to erode in a desired sequence by either reducing or increasing erosion rates. For example, regions can be treated to increase erosion rates by enhancing their chemical reactivity, e.g., coating portions of the stent with a silver coating to create a galvanic couple with the exposed, uncoated Iron surfaces on other parts of the stent. Alternatively, regions can be treated to reduce erosion rates, e.g., by using coatings.

A coating can be deposited or applied over the surface of stent to provide a desired function. Examples of such coatings include a tie layer, a biocompatible outer coating, a radiopaque metal or alloy, and/or a drug-eluting layer.

A stent can be incorporated with at least one releasable therapeutic agent, drug, or pharmaceutically active compound to inhibit restenosis, such as paclitaxel, or to treat and/or inhibit pain, encrustation of the stent or sclerosing or necrosing of a treated lumen. The therapeutic agent can be a genetic therapeutic agent, a non-genetic therapeutic agent, or cells. The therapeutic agent can also be nonionic, or anionic and/or cationic in nature. Examples of suitable therapeutic agents, drugs, or pharmaceutically active compounds include anti-thrombogenic agents, antioxidants, anti-inflammatory agents, anesthetic agents, anti-coagulants, and antibiotics, as described in Truong U.S. Pat. No. 5,674,242 and U.S. Patent Publication Nos. 2003-0003220, 2005-0251249, and 2003-0185895, the entire disclosure of each of which is herein incorporated by reference. Representative conventional approaches disperse the therapeutic agent, drug, or a pharmaceutically active compound in a polymeric coating carried by a stent. In the present invention, the therapeutic agent, drug, or a pharmaceutically active compound can be directly incorporated into the pores generated by plasma immersion ion implantation treatment on the surface of a stent, thereby eliminating the use of extra coatings.

The MOF materials described above can be used for the entire stent body, or a portion of the stent body or as a layer on a stent made of another material, or can include a layer of another material, which other material may be bioerodible or biostable, a metal, a polymer or a ceramic. The stent can include in addition to the materials described above, iron or an alloy thereof. In some embodiments, the stent can include one or more bioerodible metals, such as magnesium, zinc, iron, or alloys thereof. The stent can include bioerodible and non-bioerodible materials. The stent can have a surface including bioerodible metals, polymeric materials, or ceramics. The stent can have a surface including an oxide of a bioerodible metal. Examples of bioerodible alloys also include magnesium alloys having, by weight, 50-98% magnesium, 0-40% lithium, 0-1% iron and less than 5% other metals or rare earths; or 79-97% magnesium, 2-5% aluminum, 0-12% lithium and 1-4% rare earths (such as cerium, lanthanum, neodymium and/or praseodymium); or 85-91% magnesium, 6-12% lithium, 2% aluminum and 1% rare earths; or 86-97% magnesium, 0-8% lithium, 2-4% aluminum and 1-2% rare earths; or 8.5-9.5% aluminum, 0.15%-0.4% manganese, 0.45-0.9% zinc and the remainder magnesium; or 4.5-5.3% aluminum, 0.28%-0.5% manganese and the remainder magnesium; or 55-65% magnesium, 30-40% lithium and 0-5% other metals and/or rare earths. Bioerodible magnesium alloys are also available under the names AZ91D, AM50A, and AE42. Other bioerodible alloys are described in Bolz U.S. Pat. No. 6,287,332 (e.g., zinc-titanium alloy and sodium-magnesium alloys); U.S. Patent Publication No. 2002-000406; and Park, Science and Technology of Advanced Materials, 2, 73-78 (2001), the entire disclosure of each of which is herein incorporated by reference. In particular, Park describes Mg—X—Ca alloys, e.g., Mg—Al—Si—Ca, Mg—Zn—Ca alloys. Examples of bioerodible polymers include polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly-L-lactide, poly-D-lactide, polyglycolide, poly(alpha-hydroxy acid), and combinations thereof.

A stent can also include non-bioerodible materials. Examples of suitable non-bioerodible materials include stainless steels, platinum enhanced stainless steels, cobalt-chromium alloys, nickel-titanium alloys, noble metals and combinations thereof. In some embodiments, stent 20 can include bioerodible and non-bioerodible portions. In some embodiments, non-bioerodible or biostable metals can be used to enhance the X-ray visibility of bioerodible stents. The bioerodible main structure of a stent can be combined with one or more biostable marker sections. The biostable marker sections can include, for example, Gold, Platinum or other high atomic weight elements. The biostable marker sections can provide enhance visibility and radiopacity and can provide a structural purpose as well.

A stent can have any desired shape and size (e.g., superficial femoral artery stents, coronary stents, aortic stents, peripheral vascular stents, gastrointestinal stents, urology stents, and neurology stents). Depending on the application, stent 20 can have an expanded diameter of about 1 mm to about 46 mm. For example, a coronary stent can have an expanded diameter of about 2 mm to about 6 mm; a peripheral stent can have an expanded diameter of about 5 mm to about 24 mm; a gastrointestinal and/or urology stent can have an expanded diameter of about 6 mm to about 30 mm; a neurology stent can have an expanded diameter of about 1 mm to about 12 mm; and an abdominal aortic aneurysm stent and a thoracic aortic aneurysm stent can have an expanded diameter of about 20 mm to about 46 mm. Stent 20 can be self-expandable, balloon-expandable, or a combination of self-expandable and balloon-expandable (e.g., as described in Brittingham U.S. Pat. No. 5,366,504). Stent 20 can have any suitable transverse cross-section, including circular and non-circular (e.g., polygonal such as square, hexagonal or octagonal).

A stent can be implemented using a catheter delivery system. Catheter systems are described in, for example, Wang U.S. Pat. No. 5,195,969; Hamlin U.S. Pat. No. 5,270,086; and Raeder-Devens U.S. Pat. No. 6,726,712, the entire disclosure of each of which is herein incorporated by reference. Commercial examples of stents and stent delivery systems include Radius®, Symbiot® or Sentinol® system, available from Boston Scientific Scimed, Maple Grove, Minn.

A stent can be a part of a covered stent or a stent-graft. For example, a stent can include and/or be attached to a biocompatible, non-porous or semi-porous polymer matrix made of polytetrafluoroethylene (PTFE), expanded PTFE, polyethylene, urethane, or polypropylene. In addition to vascular lumens, a stent can be configured for non-vascular lumens. For example, it can be configured for use in the esophagus or the prostate. Other lumens include biliary lumens, hepatic lumens, pancreatic lumens, uretheral lumens and uretheral lumens. MOFs as discussed above, e.g. as a layer for drug delivery, can be utilized on other implantable medical devices such as pacing and defibrillation leads.

All references, such as patent applications, publications, and patents, referred to herein are incorporated by reference in their entirety.

Still further embodiments are in the following claims.

What is claimed is:
1. A stent comprising:
   a tubular body comprising a substrate and a coating on the substrate,
   the coating comprising a first layer of coating and a second layer of coating different from the first layer, the first layer of coating comprising a first metal-organic framework (MOF), which adjusts pore size upon desorption or adsorption of organic molecules, and a first therapeutic agent stored in the first MOF, the second layer of coating comprising a second MOF and a second therapeutic agent stored in the second MOF, the first MOF being different from the second MOF or the first therapeutic agent being different from the second therapeutic agent, and the first and second therapeutic agents to be released with different release profiles.

2. The stent of claim 1 wherein the first MOF or the second MOF has a loading weight ratio of about 1:1 or greater of the first therapeutic agent to the first MOF or of the second therapeutic agent to the second MOF.

3. The stent of claim 1 wherein the coating has a thickness of about 1 micron or less.

4. The stent of claim 1 wherein the substrate is biostable.

5. The stent of claim 1 wherein the substrate is bioerodible.

6. The stent of claim 5 wherein the substrate comprises Fe or Mg.

7. The stent of claim 5 wherein the coating is bioerodible.

8. The stent of claim 7 wherein the coating has bioerodible ligands.

9. The stent of claim 1 wherein the first MOF or the second MOF comprises ligands that are lactate, glycolate, caprolactone or amino acid, terephthalate or alkoxides.

10. The stent of claim 1 wherein the first MOF or the second MOF is hydrophobic.

11. The stent of claim 1 wherein the first therapeutic agent is effective to reduce thrombosis and the second therapeutic agent is effective to reduce restenosis, the second therapeutic agent being released after the first therapeutic agent.

12. The stent of claim 1 wherein the first and second therapeutic agents are released simultaneously.

13. The stent of claim 12 wherein the first and second therapeutic agents are released substantially in sequence.

14. The stent of claim 1 wherein one of the first and second therapeutic agents is a gas.

15. The stent of claim 14 wherein the gas comprises hydrogen, hydrogen sulfide, or Xe.

16. The stent of claim 1 wherein the first MOF or the second MOF includes Ti, Zr, Ta, Ru or Pt, Gd, Mn, Ba, Pt or Ir.

17. The stent of claim 1, wherein the first and second therapeutic agents are non-gas solids.

18. A method comprising:
forming a tubular body comprising a substrate, and
forming a coating on the substrate, wherein forming the coating comprises:
forming a first layer of the coating comprising a first metal-organic framework (MOF) that provides a high hydrogen bonding energy and that adjusts pore size upon desorption or adsorption of organic molecules;
loading the first MOF with a first therapeutic agent;
forming a second layer of the coating comprising a second MOF, the second layer being different from the first layer; and
loading the second MOF with a second therapeutic agent, the first MOF being different from the second MOF or the first therapeutic agent being different from the second therapeutic agent, and the first and second therapeutic agents to be released with different release profiles.

19. The method of claim 18, wherein the first MOF is porous and the high hydrogen bonding energy is provided by reducing pore sizes.

20. The method of claim 19, wherein reducing pore sizes comprises catenating two or more metal-organic frameworks.

21. The method of claim 18, wherein the high hydrogen bonding energy is provided by doping the first MOF with cations or anions.

22. The method of claim 21, wherein the cations or anions comprise ammonium fluoride or lithium.

23. The method of claim 18, wherein the high hydrogen bonding energy is provided by doping the MOF with Pt or Pd.

* * * * *